(12) United States Patent
Huang et al.

(10) Patent No.: US 7,347,548 B2
(45) Date of Patent: Mar. 25, 2008

(54) METHOD AND APPARATUS FOR MEASURING A RETINAL SUBLAYER CHARACTERISTIC

(75) Inventors: David Huang, Cleveland Heights, OH (US); Ou Tan, Cleveland, OH (US); Yan Li, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 465 days.

(21) Appl. No.: 10/833,524

(22) Filed: Apr. 28, 2004

(65) Prior Publication Data

US 2005/0018133 A1   Jan. 27, 2005

Related U.S. Application Data

(60) Provisional application No. 60/467,059, filed on May 1, 2003.

(51) Int. Cl.
*A61B 3/10* (2006.01)
(52) U.S. Cl. ............... 351/205; 351/206; 351/207; 351/246
(58) Field of Classification Search ............... 351/205
See application file for complete search history.

(56) References Cited

U.S. PATENT DOCUMENTS 5,321,501 A  6/1994  Swanson et al.
6,293,674 B1  9/2001  Huang et al.
6,325,512 B1  12/2001  Wei
6,356,036 B1 *  3/2002  Zhou ........................... 315/215
7,146,983 B1 *  12/2006  Hohla et al. ................. 128/898

OTHER PUBLICATIONS

Drexler, W. et al., Ultrahigh-resolution ophthalmic optical coherence tomography, Nature Medicine, 7, 502-507 (2001).

\* cited by examiner

*Primary Examiner*—Jessica T Stultz
(74) *Attorney, Agent, or Firm*—Tarolli, Sundheim, Covell & Tummino LLP (57) ABSTRACT

Methods and systems are provided for measuring a retinal sublayer characteristic of an eye. A plurality of axial scans are performed over an area of the retina of the eye. Reflections are measured during the axial scans to determine a plurality of sets of reflection intensity values. A given set of reflection intensity values is associated with one of the plurality of axial scans. A progressive refinement boundary detection algorithm is performed using the plurality of sets of reflection intensity values to determine at least one boundary location associated with the retinal sublayer for each of the plurality of sets of reflection intensity values. The retinal sublayer characteristic is determined in response to the determined boundary locations.

30 Claims, 4 Drawing Sheets

METHOD AND APPARATUS FOR MEASURING A RETINAL SUBLAYER CHARACTERISTIC

RELATED APPLICATION

This application claims priority from U.S. provisional patent application Ser. No. 60/467,059, filed on May 1, 2003, the subject matter of which is incorporated herein by reference.

The invention described in this application was supported, at least in part, by Grant No. R24 EY130135-01 from the National Institute of Health, and thus the United States government may have certain rights in the invention.

FIELD OF THE INVENTION

The present invention relates to an apparatus and method for diagnostic evaluation of the eye and, in particular, is directed to a method and apparatus for measuring a retinal sublayer characteristic.

BACKGROUND OF THE INVENTION

Glaucoma is a leading cause of blindness in the US, characterized by a gradual loss of vision due to damage to optic nerve tissue. The ganglion cell layer (GCL) of the retina contains the cell bodies of the retinal nerve fibers, which travel through the retinal nerve fiber layer (RNFL) and coalesce at the optic nerve head (ONH) to form the optic nerve. One hallmark of glaucoma is the progressive loss of neural tissue in all these structures and consequent visual loss.

Glaucoma usually responds well to treatment, but treatment cannot restore lost neural tissue. It is thus important to diagnose the disease quickly to prevent irreversible visual loss. Glaucoma diagnostic methods can generally be classified as functional or structural. Functional tests measure how the disease is affecting the patient's visual functioning. Perimetry measurements, which indicate directly the impairment to a patient's visual field, are the current diagnostic standard. However, visual field changes may not be detectable until significant damage has been done to the RNFL. In some cases, up to fifty percent of nerve fibers can be damaged before a visual field defect can be detected by perimetry. Thus structural diagnostic techniques are likely to be more successful in glaucoma screening and in the management of early glaucoma, when irreversible visual loss can be prevented.

Structural diagnostic methods measure the loss of neural tissue due to glaucoma. Several techniques are currently available for estimating the retinal nerve fiber layer in clinical practice. Indirect ophthalmoscopy and fundus photography can be used to provide a qualitative assessment of the retinal never fiber layer. In contrast, objective methods such as confocal scanning laser ophthalmoscopy, scanning laser polarimetry, and optical scanning tomography have been developed to quantify retinal nerve fiber layer thickness across the posterior pole.

SUMMARY OF THE INVENTION

In accordance with one aspect of the present invention, a method is provided for measuring a retinal sublayer characteristic of an eye. A plurality of axial scans are performed over an area of the retina of the eye. Reflections are measured during the axial scans to determine a plurality of sets of reflection intensity values. A given set of reflection intensity values is associated with one of the plurality of axial scans. A progressive refinement boundary detection algorithm is performed using the plurality of sets of reflection intensity values to determine at least one boundary location associated with the retinal sublayer for each of the plurality of sets of reflection intensity values. The retinal sublayer characteristic is determined in response to the determined boundary locations.

In accordance with another aspect of the invention, a method is provided for measuring the thickness of a layer of interest within of a retina of an eye. A plurality of axial scans of the macular area of the retina are performed via optical coherence tomography. A given axial scan produces a corresponding set of reflection intensity values. A boundary detection algorithm is performed using the plurality of sets of reflection intensity values to determine the thickness of the layer of interest within the retina. The thickness of the layer of interest is mapped across the macular area of the retina.

In accordance with another aspect of the present invention a computer program product, recorded in a computer readable medium and operative in a data processing system, is provided for measuring the thickness of a retinal layer within of an eye. A scanner control component directs an associated scanner to conduct a plurality of axial scans of a desired area of the retina of the eye and measure a set of reflection intensity values for each axial scan. A fine boundary search component performs a progressive refinement boundary detection algorithm using the measured sets of reflection values to determine boundary locations of the retinal layer. A layer thickness mapping component maps the thickness of the retinal layer across the desired area of the retina in response to the determined boundary locations of the retinal layer.

In accordance with still another aspect of the present invention, an apparatus is provided for measuring the combined thickness of the ganglion cell layer, the nerve fiber layer, and the inner plexiform layer across the macular region of a retina of an eye. An optical coherence tomography device performs a plurality of axial scans across the macular region and measures reflections during the axial scans. A control module performs a boundary detection algorithm using the measured reflections to determine the inner boundary of the nerve fiber layer and the inner boundary of the outer plexiform layer of the retina. The control module then computes the combined thickness of the ganglion cell layer, the nerve fiber layer, and the inner plexiform layer at a plurality of locations in the macular region. Each of the plurality of locations corresponds to one of the plurality of axial scans.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
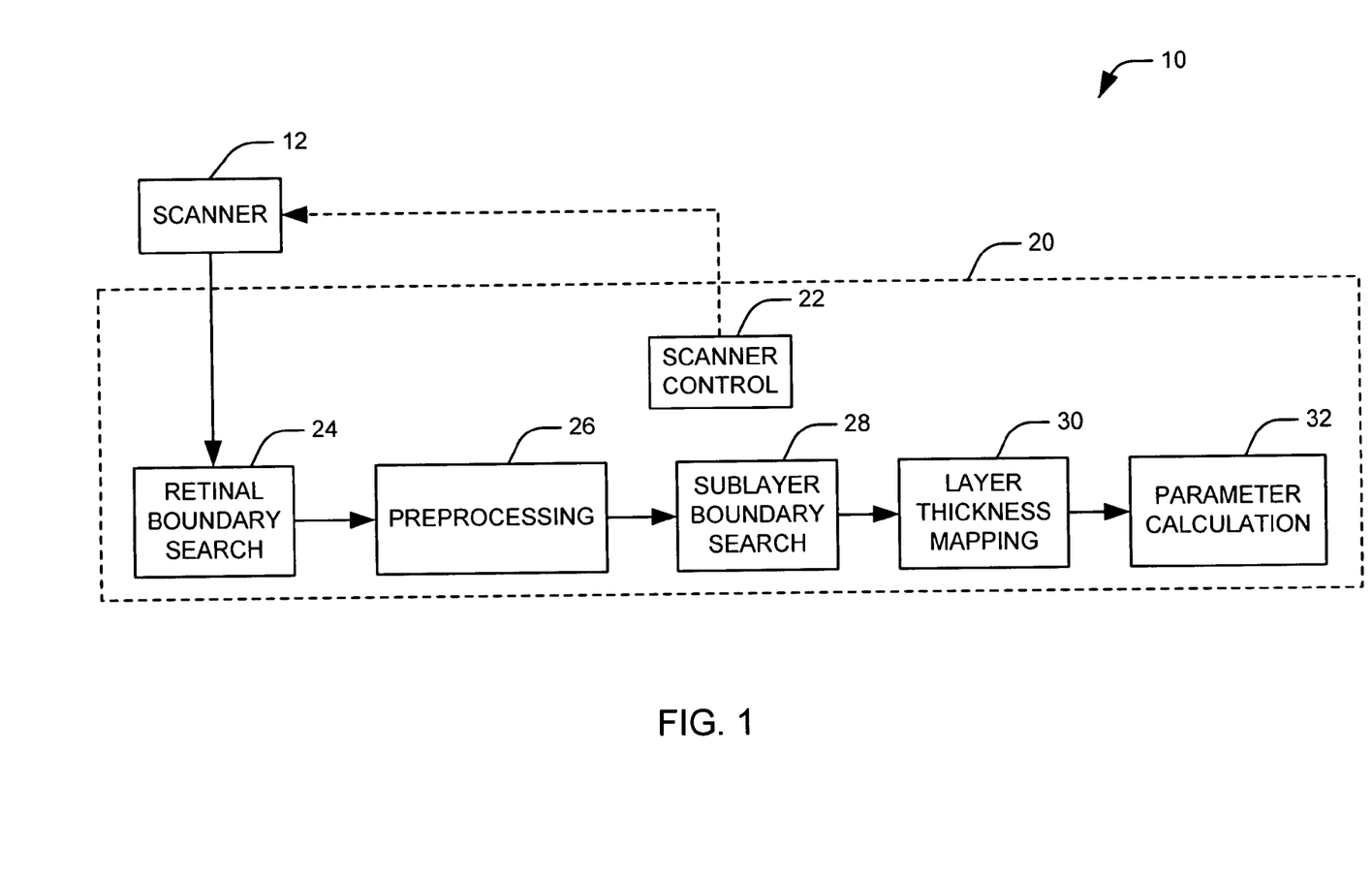
FIG. 1 illustrates an assembly for measuring one or more characteristics of a sublayer of a retina in accordance with an aspect of the present invention.

The present invention relates to an apparatus and method for diagnostic evaluation of the eye and, in particular, is directed to a method and apparatus for measuring a retinal sublayer characteristic. As representative of the present invention, FIG. 1 illustrates an assembly 10 for measuring one or more characteristics of a sublayer of a retina. The assembly includes a scanner 12 operative to perform axial scanning of a human or animal eye. The assembly further includes a control module 20 for the scanner 12 in accordance with a first embodiment of the present invention. It will be appreciated that the control module 20 and its various components can be implemented either as dedicated hardware circuitry appropriate for a described function or as computer software, recorded in a computer readable medium and operative to perform the described function when executed by a data processing system. For example, the control module can comprise a software module executed on a general purpose computer operatively connected to an appropriate scanning machine.

During an axial scan, the scanner 12 provides a beam of light, such as infrared light, to a desired location on the surface of the eye and measures the intensity and time delay of the reflected (e.g., backscattered) light. Information about the internal structure of the eye at the desired location can be determined by the intensity of the reflected light at a given time delay, with the time delay being indicative of the axial depth to which the reflected light penetrated. Specifically, the axial position of one or more boundary positions associated with retinal layers can be determined according to changes in the reflective intensity of the light at a given axial depth in the scan. In standard anatomic terminology, one directional axis is defined with respect to the center of the eyeball, with inward movement being movement toward the center of the eyeball and outward movement being movement away from the center. According to this convention, in discussing the various sublayers of the retina, the direction of increasing axial depth will be referred to as "outer" hereinafter, and the direction of decreasing axial depth will be referred to as "inner."

The control module 20 includes a scanner control component 22 that controls the operation of the scanner. The scanner control component 22 can provide the scanner 12 with a series of desired locations for scanning in accordance with a defined scan pattern. For example, one scan pattern can comprise a series of concentric circles, with scans being taken at evenly spaced points along each circle. It will be appreciated that the scanner control component 22 can control the OCT scanner 12 directly or can cooperate with an existing control device or program for the OCT scanner 12 to set the desired scan location.

The scan data for each desired location is provided to a retinal boundary search component 24. The retinal boundary search component 24 provides a preliminary location of one or more retinal sublayer boundaries in each axial scan to aid in further searching. For example, the retinal boundary search component 24 can determine inner boundaries for the nerve fiber layer (NFL) and the retina pigment epithelium (RPE), which provide approximate outer boundaries of the retina. These regions provide reflections of particularly high intensity, and their associated boundaries can generally be located with some precision via an appropriate boundary segmentation process, such as a gradient search. It will be appreciated that the data from the plurality of axial scans can be filtered, across neighboring scans, for example, to eliminate peaks that vary significantly from the norm.

Once the preliminary boundaries have been located for each axial scan, the plurality of axial scans are provided to a preprocessing component 26. The preprocessing component 26 prepares each axial scan for further processing. For example, the various scans can be aligned with a standard reference, such as the determined RPE boundary, to allow extraneous effects, such as eye movement and the incident angle of the scanner beam, to be removed. The preprocessing component 26 can also detect and compensate for shadows in the high reflectivity regions (e.g., the RPE) caused by nearby blood vessels. A low pass filter can be applied across the various axial scans to reduce speckle noise within the scan data.

The preprocessed data is then provided to a sublayer boundary search component 28. The sublayer boundary search component 28 locates desired retinal sublayer boundaries in each of the axial scans. For example, appropriate boundaries for interior retinal sublayers, such as the inner plexiform layer (IPL), the ganglion cell layer (GCL), and the outer plexiform layer (OPL) can be determined for each axial scan at the sublayer boundary search component 28 according to a progressive gradient search process. It will be appreciated that while appropriate boundaries are determined for each individual scan, data from all of the axial scans can be used in each boundary search.

Once the boundaries have been determined for each retinal sublayer of interest, the thicknesses of the retina sublayers can be determined at the associated location of each axial scan at a layer thickness mapping component 30. In an exemplary embodiment, the pattern of axial scans provided by the scanner control component 22 can be designed to evenly spread the axial scans across an area of interest, such as the macula region of the eye. Accordingly, from the sublayer boundary locations determined at each of these evenly spaced axial measurements, the layer thickness mapping component 30 can interpolate between the available values and produce a two-dimensional mapping of the thickness of a given sublayer across the area of interest. This provides an accessible diagnostic tool for quickly evaluating the extent neural tissue loss in the area of interest.

Once appropriate sublayer widths have been determined, a parameter calculation component 32 can calculate appropriate diagnostic parameters. Exemplary diagnostic parameters include the mean thickness of the retina in a given eye, the root mean square of the summed differences between corresponding axial scans in the left and right eye, and the root mean square of the summed differences between a given eye and an ideal, non-diseased eye. It will be appreciated that these parameters can be used to characterize neural tissue loss in the eye in a standardized fashion for research and diagnostic purposes.

Figure 2:
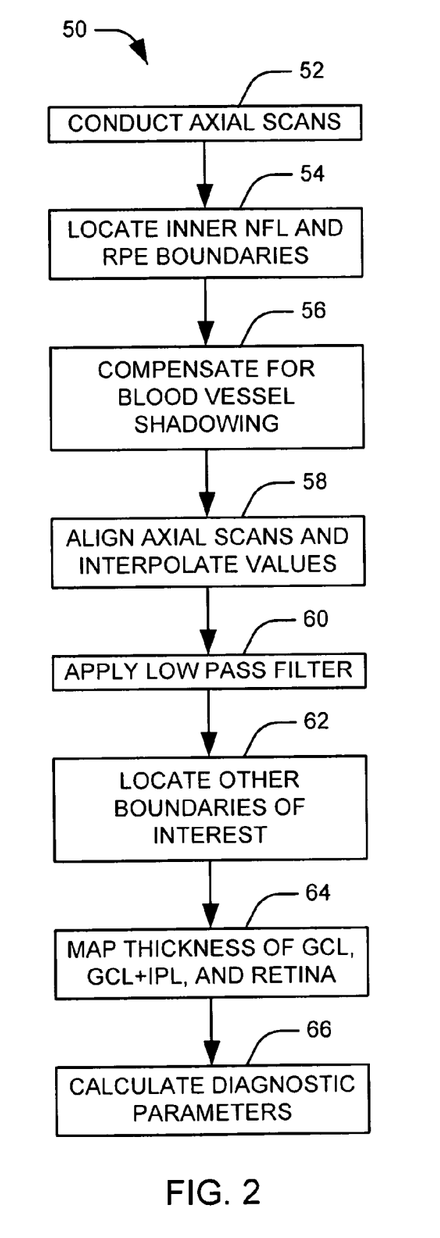
FIG. 2 illustrates an exemplary method for measuring a characteristic of a retinal sublayer in accordance with an aspect of the present invention.

FIG. 2 illustrates an exemplary method 50 for measuring a characteristic of a retinal sublayer. In the exemplary method, the widths of the GCL, the IPL, the NFL, the combined GCL and IPL, and the retina as a whole are measured in the macular regions of the retinas of a human subject to diagnose the possible onset of glaucoma. Aberrations in the width of the measured sublayers indicate a loss of neural tissue with in retina, one signature characteristic of glaucoma. It will be appreciated, however, that the described method can be adapted for use in measuring other retinal characteristics, as might be desirable for research or for the diagnosis of other disorders. It will further be appreciated that the described method is not limited to the human eye, and can be adapted for use with other species, as might be desirable for animal research or for veterinary practice.

The method 50 begins at step 52, where a plurality of axial scans are taken across an area of interest associated with the retina of each eye. In the exemplary embodiment, the areas of interest comprise the macula regions of the retinas. It will be appreciated, however, that the illustrated method 50 is not limited to the macula region and that other regions of the retina can be evaluated in accordance with the present invention. The scans can be distributed as to provide useful diagnostic information about the area of interest, with each scan having an associated location within a coordinate system defined for the area of interest. A number of different scan patterns can be utilized, according to the desired application.

In the illustrated method, each of the scans is performed via optical coherence tomography (OCT). OCT can be conceptualized as the optical analog of ultrasound. In order to generate an axial scan, a focused beam of light, typically infrared light, is directed at the tissue. The reflection time delay and the magnitude of reflected light pulse are then measured to construct an axial scan, with the reflection time delay representing a degree of axial depth. Thus the reflectivity of the tissue at a given depth can be determined, with sharp changes in reflectivity indicating boundaries between various tissue layers. The time delay can be determined with precision through the use of multiple light beams in an interferometery arrangement. A commercial available retinal scanner, such as the Optical Coherence Tomography System Model 3000 from STRATUS, can be used to perform the scans. For retina scanning, the STRATUS OCT scanner has an axial resolution of 9-10 microns (Full-width at half maximum), and an axial scan repetition rate of 400 Hz for a scan range of 2 mm.

Figure 3:
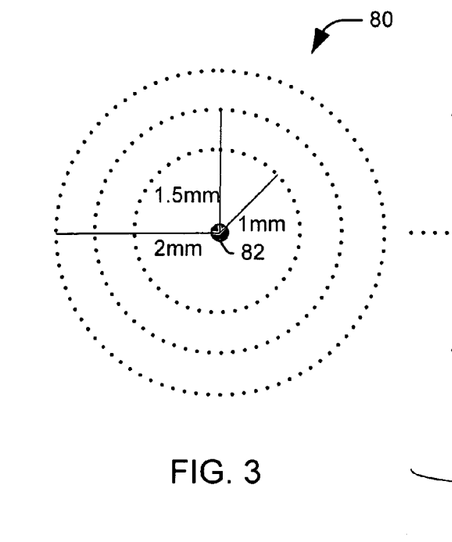
FIG. 3 illustrates a first exemplary scan pattern for the macular region of the retina in accordance with an aspect of the present invention.

FIG. 3 illustrates a first exemplary scan pattern 80 for the macula region, comprising a plurality of discrete scans arranged in concentric rings of varying diameter centered on the fovea 82. It will be appreciated that the illustrated scan pattern is simplified for the purpose of illustration and that actual scan patterns can contain many more axial scans in each circle. For example, one set of scans, with a scan duration of less than one and a half seconds, can include one hundred thirty axial scans on the inner circle, one hundred ninety axial scans on the middle circle, and two hundred fifty-eight axial scans on the outer circle. In the illustrated scan pattern 80, the three concentric circular scans can have diameters of two millimeters, three millimeters, and four millimeters, allowing for a detailed examination of the parafoveal and perifoveal regions of the retina. Circular scans with different radii can evaluate the retinal sublayer thicknesses at different locations on the retina. One advantage of the concentric circle arrangement is that the thicknesses of the retinal sublayers are relatively uniform for each circle. The illustrated pattern 80 also avoids the location of large blood vessels in the eye.

Figure 4:
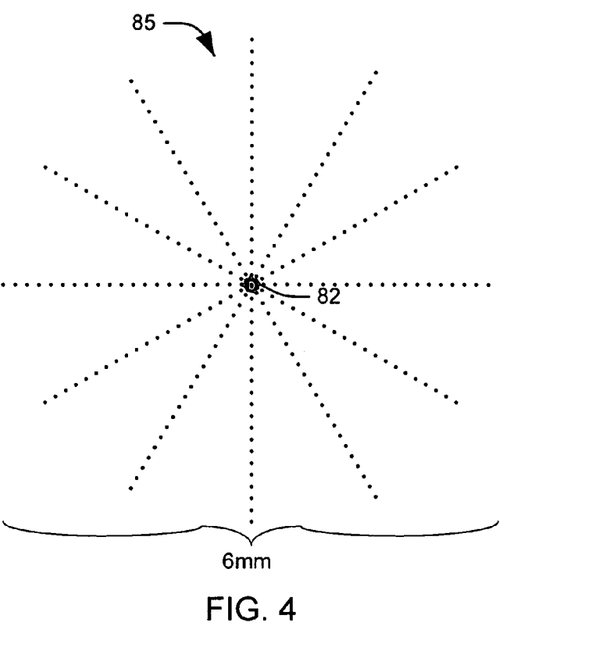
FIG. 4 illustrates a second exemplary scan pattern for the macular region of the retina in accordance with an aspect of the present invention.

FIG. 4 illustrates a second exemplary scan pattern 85 for the macula region, wherein the axial scans are arranged in a radial scan pattern comprising a plurality of lines evenly spaced in a circular pattern and passing through the fovea 82 at their mid-point. In the illustrated example, the radial scan pattern comprises six line scans arranged in a radial pattern at increments of thirty degrees. The illustrated pattern 85 covers a larger area than the concentric circle scan and provides a finer resolution in the radial direction. It is possible, however, that small areas of neural tissue loss will be missed due to the large gaps between the various lines toward the periphery of the pattern.

Figure 5:
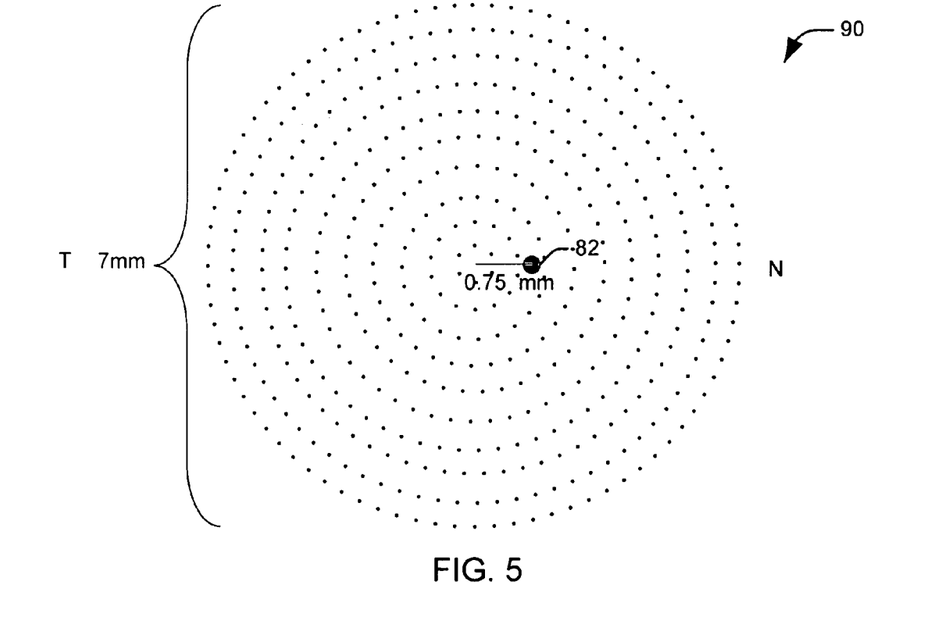
FIG. 5 illustrates a third exemplary scan pattern for the macular region of the retina in accordance with an aspect of the present invention.

FIG. 5 illustrates a third exemplary scan pattern 90 for the axial scans, wherein the axial scans are arranged in an evenly spaced grid pattern. The illustrated pattern 90, referred to hereinafter as the macular grid seven pattern, also uses a plurality of concentric rings, but the axial scans are evenly spaced both within the circles and between the circles to create a grid pattern. The illustrated pattern 90 has a diameter of seven millimeters and a center that is offset by three-quarters of a millimeter from the fovea 82 in the direction of the temple. The patterns for each eye are mirror symmetrical. The macular grid seven pattern provides a balance between the concentric circle approach and the radial approach, with good resolution in both the radial and the angular directions.

Once a pattern of scans has been completed, the method advances to step 54, where initial boundaries are located within each axial scan. This can be accomplished via a boundary segmentation algorithm, such as a gradient search or a similar process. In the illustrated method, the initial boundaries comprise the inner boundary of the nerve fiber layer (NFL) of the retina and the inner boundary of the inner choroids retina signal complex (ICORSC). These boundaries are determined at an early stage in the analysis of the OCT axial scans because they are easy to locate relative to the other sublayer boundaries. The ICORSC is represented by a large region of high reflectivity on an axial scan, with its inner portion, the retina pigment epithelium (RPE), being discernable by the contrast between the high reflectivity ICORSC and a relatively low reflectivity region between the RPE and the outer plexiform layer (OPL). Similarly, the NFL is represented by a smaller high reflectivity region near the inner portion of the retina.

Figure 6:
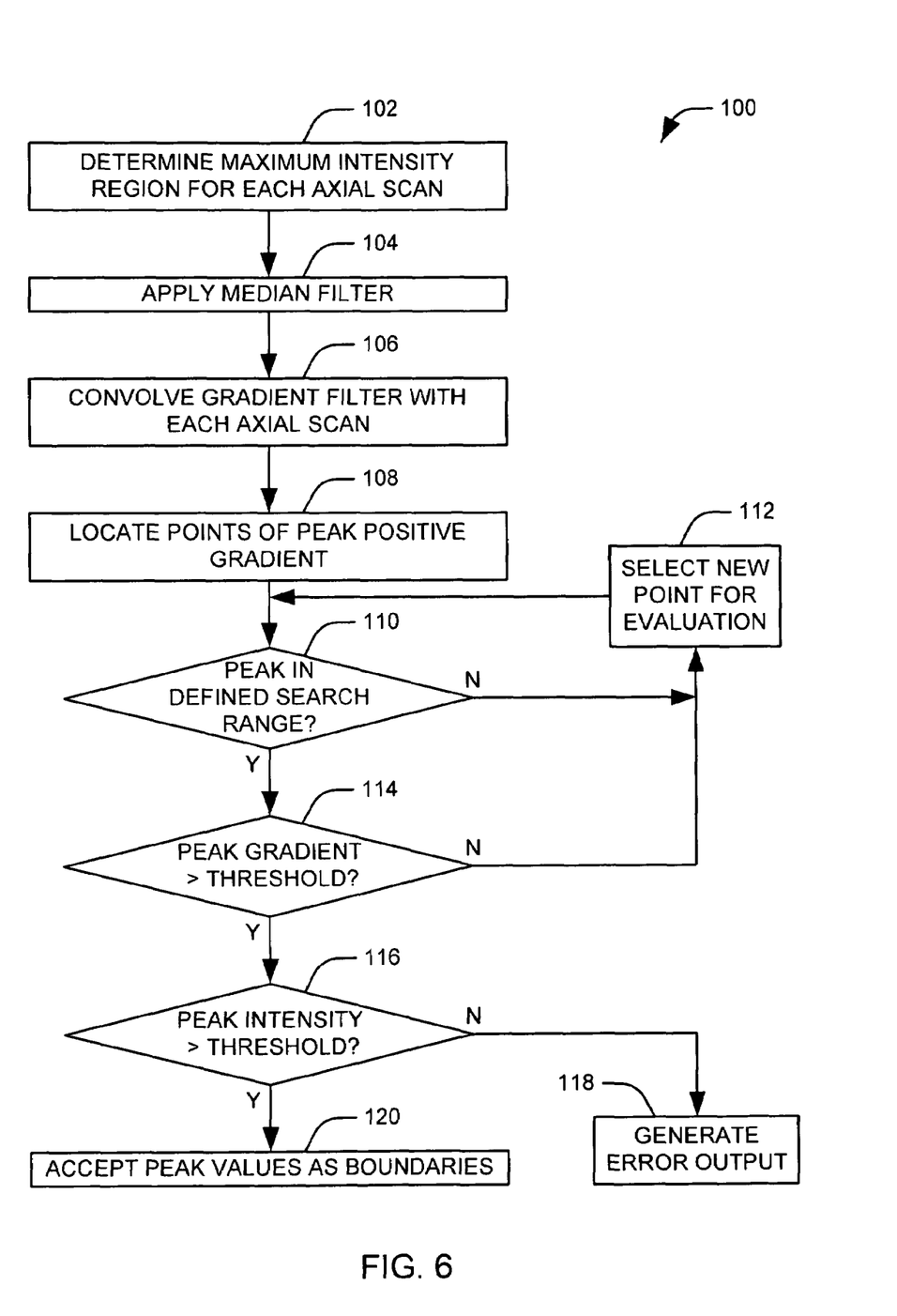
FIG. 6 illustrates an exemplary initial boundary segmentation method in accordance with an aspect of the present invention.

FIG. 6 illustrates an exemplary initial boundary segmentation method 100 in accordance with an aspect of the present invention. The illustrated method 100 determines the axial position of the inner boundary of the nerve fiber layer (NFL) of the retina and the inner boundary of the inner choroids retina signal complex (ICORSC) for a given axial scan from a plurality of axial scans. The method begins at step 102, where an axial location of greatest reflective intensity is determined for each axial scan. The maximum reflectivity will generally be found at a location corresponding to the ICORSC sublayer. Unfortunately, speckle noise in the axial scan can create regions of high intensity in other portions of the scan image.

To eliminate the outlying values, a median filter is applied across the locations determined for the axial scans at step 104. For example, in the macular seven grid pattern of scans, the median filter can be applied across circular groups of scans, a given group comprising a center scan and every scan within a determined radius. The concentric circle and radial patterns can operate similarly, with locations for a number of scans on either side of a given scan on its associated circle or line being utilized. The total number of depth values utilized in the filtering (i.e., the order of the filter) can vary with the application. The filtered location for the axial scan is referred to as the refined maximum position.

At step 106, a gradient filter is applied in the axial direction to the reflectivity values associated with the axial scan. The gradient filter is convolved with the axial scan to facilitate the location of the points of maximum gradient. The two positions of peak positive gradient are then located at step 108. In general, the position of maximum positive gradient provides a candidate for the inner RPE boundary and the position having the smaller of the two gradient values provides a candidate for the inner NFL boundary, although the gradient of the NFL boundary can exceed the gradient of the RPE boundary in some scans. The points represent transitions from relatively low reflectivity regions to relatively high reflectivity regions, as would be found at the inner boundaries of the RPE and the NFL. The method then advances to step 110, where it is determined if the gradient peaks are within a defined range of axial depths expected for the desired boundaries. For example, an appropriate range for the inner boundary of the RPE can be a window of approximately one-hundred micrometers around the refined maximum position. An appropriate range for the inner boundary of the NFL can be any point inward of the maximum position. The system can determine if an innermost of the two gradient peak locations are in the appropriate range for the NFL boundary and if the outermost of the two peaks is in the appropriate range for the RPE boundary.

If one or more of the selected boundaries are not within an appropriate range (N), the method proceeds to step 112, where one or more new gradient peak locations are selected for analysis. For example, an appropriate number of remaining peak locations having the largest positive gradient values can be selected for consideration. The process then returns to step 110 to evaluate the new peak location. If the boundaries are determined to be within the defined ranges (Y), the method advances to step 114. At step 114, it is determined if the selected peak locations have associated intensities above a threshold intensity value. The threshold intensity value is defined as the product of the maximum intensity and an intensity constant, IMAX, which varies on a range between zero and one according to the specifics of the scanning machine and the application. An appropriate constant can be determined through experimentation for a given scanning arrangement.

If one or more of the selected peak positions have intensity values less than the threshold, (N), the method proceeds to step 112, where one or more new gradient peak locations are selected for analysis. If the associated intensity values of the peak positions both exceed the threshold intensity value (Y), the method advances to step 116. At step 116, it is determined if the selected peak locations have associated gradient values above a threshold gradient value. The threshold gradient value is defined as the product of the maximum gradient in the scan and a gradient constant, GMAX, which varies on a range between zero and one according to the application. An appropriate constant can be determined through experimentation for a given scanning arrangement.

If one or more of the selected peak positions have gradient values less than the threshold, (N), the method proceeds to step 118, where an error output is generated. In response to the error output, the scan can be rejected for review by a human operator, the boundary values for the scan can be interpolated from neighboring scans in the scan pattern, or another, similar, approach can be utilized to obtain reasonable boundary estimates for the scan. If the associated intensity values of the peak positions both exceed the threshold gradient value (Y), the method advances to step 120, where the peak positions are accepted as the boundary locations. Specifically, the innermost of the two peak positions is accepted as the inner boundary of the NFL and the outermost of the two peak positions is accepted as the inner boundary of the RPE.

Returning to FIG. 2, once the inner boundary locations for the RPE and the NFL have been located, the method continues to step 56. At step 56, the various scans are analyzed for blood vessel shadowing on the reflective regions associated with the boundaries. The small blood vessels in retina are represented as small high reflectivity regions in the axial scan and cause low intensity areas in RPE due to the light they reflect away from the RPE. These low intensity regions can cause mistakes in further processing of the affected scans. Therefore, axial scans with blood vessel shadowing are detected and processed separately.

Axial scans having significant smaller total intensities summed across their ICORSC regions as compared with neighboring axial scans are marked as containing blood vessel shadowing. For example, the median of the summed intensity values of the neighboring scans can be determined and multiplied by a positive constant that is less than one. An appropriate constant can be determined through experimentation for a given scanning arrangement. If the summed intensity for the ICORSC on a given scan fails to meet this weighted median value, intensity data can be determined via interpolation from neighboring scans to fill the shadowed area.

The method then advances to step 58 where the various axial scans are aligned at a common reference depth to account for eye movement and the incident angle of the light beam used by the scanner. For example, in the coherent circle scan pattern or the radial pattern, each axial scan inside a given circle or line can be aligned at the determined inner boundary of the RPE. It is useful to be able to identify both angular trends and radial trends in the axial scan data. This analysis of radial trends in the data can be complicated by the fact that each of the concentric circles comprising the macular grid seven scan pattern generally contains a different number of axial scans, making it difficult to determine corresponding scans between circles. Accordingly, in the macular grid seven pattern, the alignment includes an interpolation step in which additional axial scan data is generated from nearby axial scans. By interpolating additional values at desired locations, the number of axial scans comprising each circle can be brought to a standard value, allowing each axial scan to have a unique corresponding neighbor scans on adjacent circles. Any applicable two-dimensional interpolation processes can be used, such as such as a two-dimensional linear interpolation or a bi-cubic spline interpolation. Once the additional axial scan data has been generated, the axial scan values can be aligned as described above.

The method then proceeds to step 60, where a low pass filter is applied across the intensity values of the various aligned axial scans. Where the concentric circle scan pattern or the radial scan pattern is used, a two-dimensional low-pass filter can be applied to the aligned OCT image to reduce speckle noise. For example, the filter can be applied in the transverse (e.g., along a line or circle of the scan pattern) and axial directions. For the macular grid seven scan, a three-dimensional low-pass filter can be applied to the interpolated OCT image to reduce the speckle noise. For example, the filter can be applied axially, and in two transverse directions, an angular direction (e.g., around a given circle), and a radial direction (e.g., between the circles). In an exemplary implementation, the low pass filter can be made wider in the transverse directions than in the axial direction, under the assumption that the boundary of each layer should be smooth once the axial scans have been aligned.

The method then advances to step 62, where the retinal sublayer boundaries of interest are determined via a boundary segmentation algorithm. In an exemplary embodiment, the boundaries of interest can include the outer boundaries of the nerve fiber layer (NFL), the inner plexiform layer (IPL), and the outer plexiform layer (OPL), as well as the inner boundaries of the IPL and NFL. Any of a number of algorithms can be used for this boundary segmentation, including region based segmentation algorithms, edge detection algorithms, and similar segmentation algorithms utilized in image processing.

Figure 7:
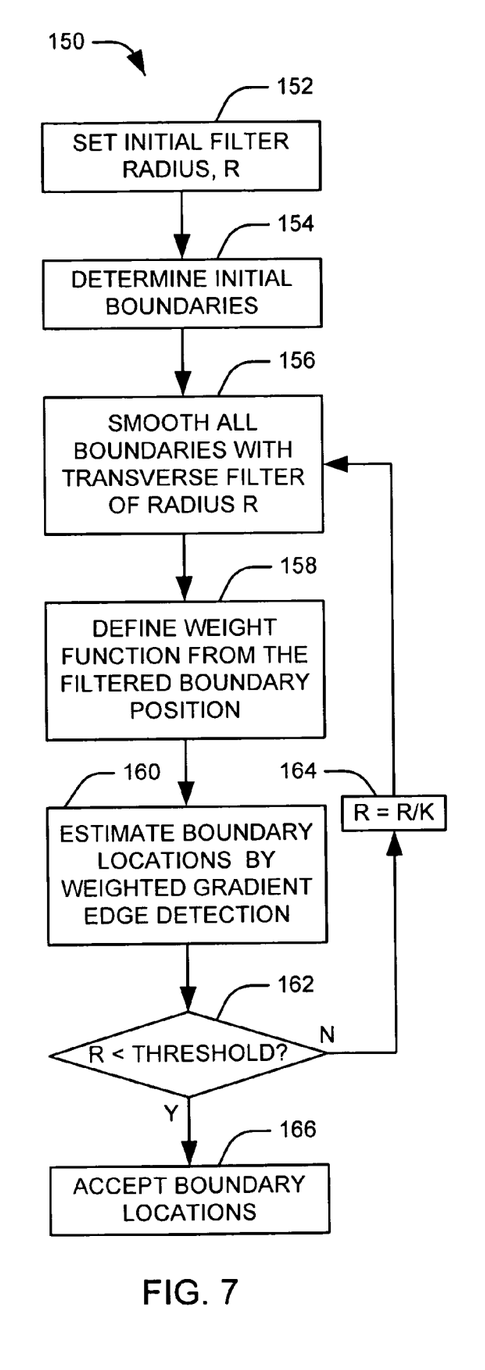
FIG. 7 illustrates an exemplary fine boundary segmentation method in accordance with an aspect of the present invention.

FIG. 7 illustrates an exemplary fine boundary segmentation method 150 in accordance with an aspect of the present invention. The illustrated method 150 determines the axial position of a retinal sublayer boundary at each of a plurality of locations within a scan pattern, with each location represented by a set of axial scan data. The sets of axial scan data can be obtained via scanning or interpolated from other values. The illustrated method can be used with the macular grid seven scan pattern and is described in relation to that pattern for the purpose of example. It will be appreciated, however, that the method is adaptable to other scan patterns, including the concentric circle scan pattern, the radial pattern, and other patterns not herein described.

The method begins at step 152, where an initial value for the filter radius, R, is determined. The filter radius defines, for a given axial scan, a number of neighboring axial scans that will be utilized in a low pass filtering of the scan data. The method then proceeds to 154, where an initial axial depth of interest is determined for each axial scan via a gradient search. Generally, the boundary will represent a gradient peak or trough within the axial scan intensity data, and the specific peak or trough can be selected according to knowledge of the position of the sublayer relative to other retina sublayers and its known reflective properties.

Once an initial boundary depth has been determined for each axial scan, the method advances to step 156, where a low pass filter of radius R is applied to the depth values. This has the effect of smoothing the determined boundaries across the axial scans. The method then advances to step 158, where a weight function is generated for each axial scan according to its filtered boundary depth value and the width of the filter. For example, a normalized Gaussian function can be computed for a given axial scan with a mean equal to the determined axial depth of the boundary and a standard deviation derived from the filter width.

Once the weight function has been computed, a weighted gradient search is conducted at step 160. In conducting the weighted gradient search, the gradient values are weighted according to the generated weight function. A peak or trough value is then determined from the weighted values according to knowledge of the position of the sublayer relative to other retina sublayers and its known reflective properties. Once a new value has been obtained, the method advances to step 162, where it is determined if the filter radius is less than a threshold value.

If the filter radius is not less than the threshold value (N), the method continues to step 164, where the filter radius is divided by a constant factor, K, where K is a number greater than one. A suitable value for the constant can be determined by experimentation for a given application. The method then returns to step 156 to perform another weighted gradient search. If the filter radius is less than the threshold value (Y), the method advances to step 166, where the determined boundary values for each axial scan are accepted. The method then terminates.

Returning to FIG. 2, once appropriate boundary values have been determined for each of the axial scans, the widths of selected retinal layers can be mapped at step 64 for analysis. Using the macular grid seven pattern, or a similarly comprehensive scan pattern, it is possible to interpolate accurate boundary values for any given location within the limits of the scan pattern. From these boundaries, appropriate widths can be calculated. In an exemplary embodiment, one or more of the width of the ganglion cell layer (GCL) (e.g., the distance between the outer boundary of the nerve fiber layer (NFL) and the inner boundary of the inner plexiform layer (IPL)), the width of the combined GCL and IPL (e.g., the distance between the outer boundary of the NFL and the outer boundary of the IPL), and the entire retina (e.g., the distance between the inner boundary of the NFL and the inner boundary of the inner choroids retina signal complex (ICORSC)) can be calculated.

Various thickness maps can be generated for a given subject using the determined boundary data. For example, thickness maps can be generated for each eye for the various layers of interest (e.g., GCL, GCL+IPL, total retina, etc.). From these, other maps can be derived showing other diagnostic parameters of interest. For example, maps can be generated showing the difference in thickness between the superior and inferior portions of each eye can be generated. A similar map of the difference in thickness between the two eyes can also be generated. One skilled in the art will appreciate other diagnostic uses for the boundary data determined by the illustrated method.

At step 64, the determined width data is used to determine one or more diagnostic parameters of interest. Each parameter can be useful for quantifying the width data from the mappings to allow for easy comparison between a plurality of subjects. One skilled in the art will appreciate that a variety of useful parameters can be derived from the width data obtained in the illustrated method. In an exemplary embodiment, six parameters are determined for each sublayer or sublayer combination of interest.

A first exemplary parameter is the mean thickness of a given layer. The mean thickness parameter is calculated as the weighted average thickness of a layer of interest. The mean thickness is calculated as:

$$MT = \frac{\int\int_A T(r, \theta) dA}{A} \quad \text{Eq. 1}$$

where, $T(r, \theta)$ is the thickness measured at position $(r, \theta)$, $r$ is the distance from position of an axial scan to the center of fovea, $\theta$ is the angle with the horizontal plane.

A second exemplary parameter is the root mean square (RMS) fraction loss. The RMS fraction loss is a measurement of the degree to which the shape of the subject's measured layer thickness departs from the normal layer thickness. It is calculated as:

$$FL(r, \theta) = \begin{cases} 0 & T(r, \theta) > N(r, \theta) \\ \dfrac{T(r, \theta) - N(r, \theta)}{N(r, \theta)} & \text{otherwise} \end{cases} \quad \text{Eq. 2}$$

$$RMSFL = \sqrt{\dfrac{\iint_A (FL(r, \theta))^2 dA}{A}}$$

where, $T(r, \theta)$ is the thickness measured at position $(r, \theta)$, $r$ is the distance from position of an axial scan to the center of fovea, $\theta$ is the angle with the horizontal plane, and $N(r, \theta)$ is the average thickness measured of normal subjects at the position $(r, \theta)$.

A third exemplary parameter is the mean superior-inferior difference (MSID). The MSID is the difference between corresponding axial scans in the superior and inferior portions of the macula and is used to detect asymmetric loss of retinal layers. The MSID is calculated as $$MSID = \dfrac{\iint_{0 < \theta < \pi} (T(r, \theta) - T(r, -\theta)) dA}{A/2} \quad \text{Eq. 3}$$

where, $T(r, \theta)$ is the thickness measured at position $(r, \theta)$, $r$ is the distance from position of an axial scan to the center of fovea, $\theta$ is the angle with the horizontal plane.

A fourth exemplary parameter is the root mean square superior-inferior difference (RMSSID). The root mean square superior-inferior difference is the roots mean square of the difference between corresponding axial scans in the superior and inferior portions of the macula. The RMSSID is calculated as:

$$RMSSID = \sqrt{\dfrac{\iint_{0 < \theta < \pi} k(r, \theta)(T(r, \theta) - T(r, -\theta))^2 dA}{A/2}} \quad \text{Eq. 4}$$

where, $T(r, \theta)$ is the thickness measured at position $(r, \theta)$, $r$ is the distance from position of an axial scan to the center of fovea, $\theta$ is the angle with the horizontal plane.

A fifth exemplary parameter is the mean left-right eye difference (MLRD). The mean left-right eye difference is simply the averaged difference between corresponding locations on the left and right eye. The mean left right eye difference is calculated as:

$$MLRD = \dfrac{\iint_A (T_{left}(r, \theta) - T_{right}(r, \theta)) dA}{A} \quad \text{Eq. 5}$$

where, $T(r, \theta)$ is the thickness measured at position $(r, \theta)$, $r$ is the distance from position of an axial scan to the center of fovea, $\theta$ is the angle with the horizontal plane.

A sixth exemplary parameter is the root mean square left-right eye difference (RSMLRD). The root mean square left-right eye difference is simply the averaged difference between corresponding locations on the left and right eye. The root mean square left right eye difference is calculated as:

$$RMSLFD = \sqrt{\dfrac{\iint_A (T_{left}(r, \theta) - T_{right}(r, \theta))^2 dA}{A}} \quad \text{Eq. 6}$$

where, $T(r, \theta)$ is the thickness measured at position $(r, \theta)$, $r$ is the distance from position of an axial scan to the center of fovea, $\theta$ is the angle with the horizontal plane.

From the above description of the invention, those skilled in the art will perceive improvements, changes, and modifications. For example, it is contemplated that the present invention could be adapted to diagnose a number of degenerative eye disorders by measuring other characteristics of various structures of the eye, both within and external to the retina. Such improvements, changes, and modifications within the skill of the art are intended to be covered by the appended claims.

Having described the invention, we claim:

1. A method for measuring a retinal sublayer characteristic of an eye, said method comprising the steps of:
    performing a plurality of axial scans over an area of the retina;
    measuring reflections during the axial scans to determine a plurality of sets of reflection intensity values, a given set of reflection intensity values being associated with one of the plurality of axial scans;
    performing an iterative boundary detection algorithm using the plurality of sets of reflection intensity values to determine at least one boundary location associated with the retinal sublayer for each of the plurality of sets of reflection intensity values, the iterative boundary detection algorithm comrrising:
    determining respective estimated boundary values from the set of reflection intensity values associated with each axial scan for the at least one boundary location associated with the retinal sublayer; and
    performing the following steps iteratively until a termination event occurs:
    applying a transverse filter to the estimated boundary values, the filter having an associated width;
    generating a weight function from the estimated boundary values;
    determining respective new estimated boundary values from the plurality of sets of reflection intensity values, a given boundary being determined as an extrema on a gradient map of an associated set of reflection intensity values, the gradient map being weighted by the weight function; and
    reducing the associated width of the transverse filter; and
    determining the retinal sublayer characteristic in response to the determined boundary locations.

2. The method of claim 1, further comprising the step of locating the inner and outer boundaries of the retina at each axial scan via a gradient search using the associated set of reflection intensity values.

3. The method of claim 1, further comprising the step of correcting the set of reflection intensity values at each axial scan for shadowing caused by blood vessels near the at least one boundary location.

4. The method of claim 1, the step of performing a plurality of axial scans including performing a plurality of axial scans using optical coherence tomography.

5. The method of claim 1, wherein the plurality of axial scans are arranged in a plurality of concentric circles, the scans being substantially evenly spaced around and between the plurality of concentric circles to form a grid pattern across the area of the retina.

6. The method of claim 1, further comprising the step of calculating at least one diagnostic parameter from the retinal sublayer characteristic, the diagnostic parameter being indicative of the progress of glaucoma within the eye.

7. The method of claim 1, wherein the area of the retina is the macular area of the retina.

8. A method for measuring the thickness of a layer of interest within of a retina of an eye, said method comprising the steps of:
performing a plurality of axial scans of the macular area of the retina via optical coherence tomography, a given axial scan producing a corresponding set of reflection intensity values;
performing a boundary detection algorithm using the plurality of sets of reflection intensity values to determine the thickness of the layer of interest within the retina;
mapping the thickness of the layer of interest across the macular area of the retina; and
calculating at least one diagnostic parameter from the determined thicknesses, the at least one diagnostic parameter comprising at least one of the mean difference in thickness between corresronding positions on the retinas of the left and right eves and the root mean square difference in thickness between corresponding positions on the superior portion of the retina and the inferior portion of the retina.

9. The method of claim 8, the layer of interest comprising the combined inner layers of the retina, the inner layers comprising the ganglion cell layer, the inner plexiform layer, and the nerve fiber layer.

10. The method of claim 8, the at least one layer of interest comprising the ganglion cell layer.

11. A computer program product, recorded in a computer readable medium and operative in a data processing system, for measuring the thickness of a retinal layer within of an eye, said computer program product comprising:
a scanner control component that directs an associated scanner to conduct a plurality of axial scans of a desired area of the retina of the eye and measure a set of reflection intensity values for each axial scan;
a sublayer boundary search component that performs an iterative boundary detection algorithm using the measured sets of reflection values to determine boundary locations of the retinal layer;
a layer thickness mapping component that maps the thickness of the retinal layer across the desired area of the retina in response to the determined boundary locations of the retinal layer; and
a parameter calculation component that calculates at least one diagnostic parameter, representing the progression of glaucoma in the eye, based on the mapped thickness of the retinal layer, the at least one diagnostic parameter comprising the root-mean square of the loss of thickness over the mapped retinal layer as compared to a defined normal thickness for the retinal layer.

12. The computer program product of claim 11, further comprising a preprocessing component that adjusts the measured sets of reflection values for blood vessel shadowing.

13. The computer program product of claim 11, further comprising a retina boundary search component that determines approximate boundaries for the retina via a gradient search.

14. The computer program product of claim 11, the retinal layer comprising the combined inner plexiform layer and the ganglion cell layer of the retina.

15. The computer program product of claim 11, the retinal layer comprising the entire retina.

16. An apparatus for measuring the thickness of a retina layer, comprising:
an optical coherence tomography device; and
a general purpose computer, operatively connected to the optical coherence tomography device, that executes the computer program product of claim 11.

17. An apparatus for three-dimensional scanning of the macular region of a retina of an eye, said apparatus comprising:
an optical coherence tomography device; and
a control module that directs the optical coherence tomography device to perform a plurality of axial scans to obtain axial intensity data for a corresponding plurality of scan locations within the macular region, the scan locations being arranged in a plurality of concentric circles and substantially evenly spaced around and between the plurality of concentric circles to form a grid pattern across the macular region, and performs a boundary detection algorithm using the reflection data for the plurality of scan locations to determine the thickness of a retinal sublayer of interest within the retina, the boundary detection algorithm comprising the steps of:
determining respective estimated boundary values from the intensity data associated with each scan location for at least one boundary location associated with the retinal sublayer; and
performing the following steps iteratively until a termination event occurs:
applying a transverse filter to the estimated boundary values, the filter having an associated width;
generating a weight function from the estimated boundary values;
determining respective new estimated boundary values from the intensity data associated with each scan location, a given boundary being determined as an extrema on a gradient map of the intensity data, the gradient map being weighted by the weight function; and
reducing the associated width of the transverse filter.

18. The apparatus of claim 17, the control module calculating at least one diagnostic parameter, indicative of the progression of glaucoma within the eye, from the determined thickness values.

19. The apparatus of claim 17, wherein the retinal sublayer of interest comprises a combination of the ganglion cell layer and the inner plexiform layer.

20. The method of claim 8, wherein the plurality of axial scans are substantially evenly over two dimensions as to form a grid pattern across the macular area.

21. The method of claim 20, wherein the two dimensions are the polar and radial dimensions of a polar coordinate system.

22. The computer program product of claim 11, wherein the scanner control component directs the associated scanner to conduct the plurality of axial scans at associated scan locations, the associated scan locations being spaced substantially evenly over two dimensions within the desired area of the retina.

23. The computer program product of claim 22, wherein the two dimensions are the polar and radial dimensions of a polar coordinate system.

24. The computer program of claim 11, the at least one diagnostic parameter including the mean thickness of the mapped retinal layer.

25. The apparatus of claim 17, wherein the control module directs the optical coherence tomography device to perform the plurality of axial scans at associated scan locations, the associated scan locations being spaced substantially evenly over two dimensions within the macular region.

26. The apparatus of claim 25, wherein the two dimensions are the polar and radial dimensions of a polar coordinate system.

27. An apparatus for three-dimensional scanning of the macular region of a retina of an eye, said apparatus comprising:
an optical coherence tomography device; and
a control module that directs the optical coherence tomography device to perform a plurality of axial scans to obtain axial intensity data for a corresponding plurality of scan locations within the macular region, the scan locations being arranged in a plurality of concentric circles and substantially evenly spaced around and between the plurality of concentric circles to form a grid pattern across the macular region, performs a boundary detection algorithm using the reflection data for the plurality of scan locations to determine the thickness of a retinal sublayer of interest within the retina, and calculates at least one diagnostic parameter, indicative of the progression of glaucoma within the eye, from the determined thickness values, the calculated diagnostic parameter comprising at least one of the root mean square difference in thickness between corresponding positions on the macular regions of the left and right eyes and the mean difference in thickness between corresponding positions on the superior portion of the macular region and the inferior portion of the macular region.

28. The apparatus of claim 27, wherein the retinal sublayer of interest comprises a combination of the ganglion cell layer and the inner plexiform layer.

29. The apparatus of claim 27, wherein the control module performs the plurality of axial scans such that the plurality scan locations are distributed substantially evenly over two dimensions as to form a grid pattern across the macular area.

30. The apparatus of claim 29, wherein the two dimensions are the polar and radial dimensions of a polar coordinate system.

* * * * *